United States Patent
Schaub et al.

(10) Patent No.: US 9,000,227 B2
(45) Date of Patent: Apr. 7, 2015

(54) PROCESS FOR PREPARING 3-SUBSTITUTED 2-ALKENALS, IN PARTICULAR PRENAL

(71) Applicant: BASF SE, Ludwigshafen (DE)

(72) Inventors: Thomas Schaub, Neustadt (DE); Bernhard Brunner, Heidelberg (DE); Klaus Ebel, Heddesheim (DE); Rocco Paciello, Bad Dürkheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/360,323

(22) PCT Filed: Nov. 23, 2012

(86) PCT No.: PCT/EP2012/073422
§ 371 (c)(1),
(2) Date: May 23, 2014

(87) PCT Pub. No.: WO2013/076226
PCT Pub. Date: May 30, 2013

(65) Prior Publication Data
US 2014/0323770 A1 Oct. 30, 2014

Related U.S. Application Data

(60) Provisional application No. 61/563,635, filed on Nov. 25, 2011.

(30) Foreign Application Priority Data

Nov. 25, 2011 (EP) .................................... 11190852

(51) Int. Cl.
C07C 45/66 (2006.01)
C07C 45/00 (2006.01)
C07C 45/29 (2006.01)

(52) U.S. Cl.
CPC ............... *C07C 45/66* (2013.01); *C07C 45/002* (2013.01); *C07C 45/29* (2013.01)

(58) Field of Classification Search
USPC .................................................. 568/485, 489
See application file for complete search history.

(56) References Cited

U.S. PATENT DOCUMENTS 6,013,843 A 1/2000 Aquila et al.
8,367,875 B2 2/2013 Lanver et al.
(Continued)

FOREIGN PATENT DOCUMENTS

EP 0881206 A1 12/1998
EP 2130583 A1 12/2009
(Continued)

OTHER PUBLICATIONS

International Search Report for PCT/EP2012/073422 mailed Jan. 30, 2013.
Dobson et al., "Catalytic Dehydrogenation of Primary and Secondary Alcohols by $Ru(OCOCF_3)_2(CO)(PPh_3)_2$", J. Organomet. Chem. 87, pp. C52-C53 (1975).
Donati et al., "Iridium aminyl radical complexes as catalysts for the catalytic dehydrogenation of primary hydroxyl functions in natural products", Comptes Rendus Chimie 10, pp. 721-730 (2007).
Feng et al., "The functionalized poly(ethylene glycol) supported palladium nanoparticles as a highly efficient catalyst for aerobic oxidation of alcohols", Catalysis Communications 10, pp. 1542-1546 (2009).
(Continued)

*Primary Examiner* — Sikarl Witherspoon
(74) *Attorney, Agent, or Firm* — Drinker Biddle & Reath LLP

(57) ABSTRACT

The present invention to a process for preparing 2-alkenals of the formula I

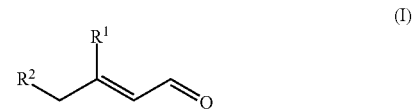

in which
$R^1$ is selected from hydrogen and $C_1$-$C_4$-alkyl; and
$R^2$ is selected from hydrogen, $C_1$-$C_{12}$-alkyl, $C_2$-$C_{12}$-alkenyl, $C_4$-$C_8$-cycloalkyl and $C_6$-$C_{10}$-aryl, wherein $C_1$-$C_{12}$-alkyl and $C_1$-$C_{12}$-alkenyl may be substituted with $C_5$-$C_7$-cycloalkyl or $C_5$-$C_7$-cylcoalkenyl;
comprising dehydrogenating an alkenol of the formula II, an alkenol of the formula III or a mixture thereof,

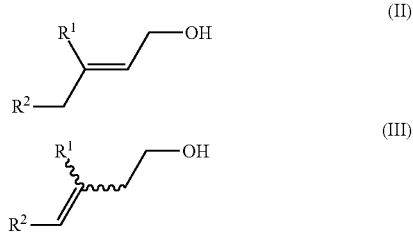

wherein
$R^1$ and $R^2$ are each as defined above,
wherein the alkenol II, the alkenol III or a mixture thereof is brought into contact with a catalytic system comprising at least one ligand and a metal compound selected from ruthenium(II) compounds and iridium(I) compounds, and
wherein the hydrogen formed during the dehydrogenation is removed from the reaction mixture by:
v) reaction with a reoxidant selected from $C_3$-$C_{12}$-alkanones, $C_4$-$C_9$-cycoalkanones, benzaldehyde and mixtures thereof; and/or
vi) purely physical means.

19 Claims, No Drawings

(56) References Cited

U.S. PATENT DOCUMENTS

| | | |
|---|---|---|
| 8,410,293 B2 | 4/2013 | Ebel et al. |
| 8,450,534 B2 | 5/2013 | Ebel et al. |
| 8,563,781 B2 | 10/2013 | Schelper et al. |
| 8,563,785 B2 | 10/2013 | Limbach et al. |
| 8,563,787 B2 | 10/2013 | Stock et al. |
| 8,609,903 B2 | 12/2013 | Klaus et al. |
| 8,637,709 B2 | 1/2014 | Schaub et al. |
| 8,648,031 B2 | 2/2014 | Ebel et al. |
| 8,697,834 B2 | 4/2014 | Schaub et al. |
| 8,703,994 B2 | 4/2014 | Schaub et al. |
| 8,741,988 B2 | 6/2014 | Klopsch et al. |
| 8,785,693 B2 | 7/2014 | Schaub et al. |
| 8,791,297 B2 | 7/2014 | Schaub et al. |
| 2010/0130758 A1 | 5/2010 | Kaneda et al. |
| 2011/0319657 A1 | 12/2011 | Schneider et al. |
| 2012/0022290 A1 | 1/2012 | Schaub et al. |
| 2012/0157711 A1 | 6/2012 | Schaub et al. |
| 2012/0203013 A1 | 8/2012 | Weyrauch et al. |
| 2012/0232293 A1 | 9/2012 | Schaub et al. |
| 2012/0232294 A1 | 9/2012 | Schaub et al. |
| 2013/0006021 A1 | 1/2013 | Limbach et al. |
| 2013/0012739 A1 | 1/2013 | Schaub et al. |
| 2013/0072726 A1 | 3/2013 | Schuch et al. |
| 2013/0090496 A1 | 4/2013 | Schaub et al. |
| 2013/0137901 A1 | 5/2013 | Strautmann et al. |
| 2013/0245132 A1 | 9/2013 | Ebel et al. |

FOREIGN PATENT DOCUMENTS

| | | |
|---|---|---|
| GB | 1061045 A | 3/1967 |
| JP | 2004033798 A | 2/2004 |
| JP | 2008214289 A | 9/2008 |
| JP | 2010184877 A | 8/2010 |
| WO | WO-2008037693 A1 | 4/2008 |
| WO | WO-2008111282 A1 | 9/2008 |
| WO | WO 2009/106621 A1 | 9/2009 |
| WO | WO-2009106621 A1 | 9/2009 |
| WO | WO-2010032770 A1 | 3/2010 |

OTHER PUBLICATIONS

Hou et al., "Supported palladium nanoparticles on hybrid mesoporous silica: Structure/activity-relationship in the aerobic alcohol oxidation using supercritical carbon dioxide", Journal of Catalysis 258, pp. 315-323 (2008).

Kaneda et al., "Heterogeneous Oxidation of Allylic and Benzylic Alcohols Catalyzed by Ru—Al—Mg Hydrotalcites in the Presence of Molecular Oxygen", J. Org. Chem. 63, pp. 1750-1751 (1998).

Kantam et al., "Aerobic Alcohol Oxidation by Ruthenium Species Stabilized on Nanocrystalline Magnesium Oxide by Basic Ionic Liquids", Adv. Synth. Catal. 350, pp. 1225-1229 (2008).

Karimi et al., "Aerobic oxidation of alcohols using various types of immobilized palladium catalyst: the synergistic role of functionalized ligands, morphology of support, and solvent in generating and stabilizing nanoparticles", Green Chemistry 11, pp. 109-119 (2009).

Larock et al., "Oxidation of Allylic Alcohols to Unsaturated Carbonyl Compounds by Ruthenium Dioxide and Dioxyged/Ruthenium Dixoxide", J. Org. Chem 49, pp. 3435-3436 (1984).

Nakano et al., "Selective Oxidation of Alcohol Function in Allylic Alcohols to cal-Unsaturated Carbonyl Compounds Catalyzed by Zirconocene Complexes", J. Org. Chem. 52, pp. 4955-4959 (1987).

Nicholson et al., "Hydrogen-transfer Catalysed by Some Group VIII Metal Complexes", Proc. Chem. Soc., pp. 282-283 (1963).

Nielsen et al., "Efficient Hydrogen Production from Alcohols under Mild Reaction Conditions", Angew. Chem., pp. 9767-9771 (2011).

Venkatesan et al., "Ruthenium-functionalized nickel hydroxide catalyst for highly efficient alcohol oxidations in the presence of molecular oxygen", Chem. Commun., pp. 1912-1914 (2009).

Yamaguchi et al., "Creation of a Monomeric Ru Species on the Surface of Hydroxyapatite as an Efficient Heterogeneous Catalyst for Aerobic Alcohol Oxidation", J. Am. Chem. Soc. 122, pp. 7144-7145 (2000).

International Preliminary Report on Patentability and Written Opinion of the International Searching Authority for PCT/EP2012/073422 dated May 27, 2014.

PROCESS FOR PREPARING 3-SUBSTITUTED 2-ALKENALS, IN PARTICULAR PRENAL

CROSS-REFERENCE TO RELATED APPLICATIONS

This application is a national stage application (under 35 U.S.C. §371) of PCT/EP2012/073422, filed Nov. 23, 2012, which claims benefit of European Application No. 11190852.1 and U.S. Provisional Application No. 61/563, 635, filed Nov. 25, 2011, all of which are incorporated herein by reference in their entirely.

The present invention relates to a process for preparing 3-substituted 2-alkenals, such as, in particular, prenal (3-methyl-2-butenal). More specifically, the invention relates to a process for preparing 3-substituted 2-alkenals by catalytic dehydrogenation of 3-substituted 2-alken-1-ols, such as prenol (3-methyl-2-buten-1-ol), and/or 3-substituted 3-alken-1-ols, such as isoprenol (3-methyl-3-buten-1-ol).

Prenal is an important precursor especially for the preparation of terpene-based fragrances, such as citral, and for the preparation of vitamins, such as vitamin E, and therefore is of great technical and economic importance.

The most common procedures for preparing prenal use prenol or isoprenol as starting materials. Thus, EP 0 881 206 describes the conversion of these starting materials via oxidative dehydrogenation using a silver catalyst in the gas phase that contains oxygen. The selectivity of this approach could be improved by further developing the catalytic system, as disclosed e.g. In WO 2008/037693. However, in order to obtain sufficient conversion rates and selectivities it is necessary to carry out the gas phase procedure at temperatures of about 360° C. while maintaining short contact times. This is required, on the one hand, to ensure adequate reactivity and, on the other hand, to prevent decomposition reactions of the sensitive reactants and products. These conditions can only be accomplished by using expensive and error-prone equipment of high complexity.

Furthermore, there are multiple reports on aerobic oxidations of prenol to prenal that are performed in a liquid phase using a heterogenic catalyst. Thus, the application of palladium nanoparticles as catalyst in such procedures is described in Catalysis Communications 10 (2009) 1542-1546, Journal of Catalysis 258 (2008) 315-323, and Green Chemistry 11 (2009) 109-119. Similar conversions of prenol to prenal using ruthenium dioxide or gold on a support as heterogenic catalysts are disclosed in J. Org. Chem. 49 (1984) 3435-3436 and in WO 2009/106621, respectively. Further liquid phase oxidations of allylic alcohols to the related aldehydes that use heterogenic catalysts are reported in WO 2010/032770, Chem. Commun. (2009) 1912-1914, Adv. Synth. Catal. 350 (2008) 1225-1229, J. Am. Chem. Soc. 122 (2000) 7144-7145 and J. Org. Chem. 63 (1998) 1750-1751.

However, the limited reactivity of the heterogenic catalyst in these reactions often requires high oxygen concentration and elevated pressures of above 10 bar in order to achieve reasonable conversion rates. If in addition the significant heat generation of the oxidative dehydrogenation is considered, it becomes evident that these reactions may cause safety engineering problems. Moreover the reactants (prenol or isoprenol) as well as the products (prenal or isoprenal) are labile at higher temperatures and/or in the presence of oxygen. Hence the aforementioned reaction conditions lead to a rise of secondary reactions resulting in reduced selectivities.

The latter problems can be avoided by conducting the dehydrogenation under anaerobic conditions as this results in a considerably lower generation of heat. However, the hydrogen originating from respective reactions threatens to hydrogenate double bonds which are present in the reactants and/or products. In case of the conversion of prenol or isoprenol that would lead to the formation of isoamyl alcohol (3-methylbutan-1-ol) and isovaleraldehyde (3-methylbutanal). Because of this difficulty there are only a few reports in the prior art on anaerobic dehydrogenations of these substrates. For example WO 2008/111282 discloses the heterogenic dehydrogenation of prenol to prenal using hydrotalcite-supported silver, copper or gold catalysts. The disadvantage of these catalysts is that the high basicity of the hydrotalcite causes secondary reactions of the C—H acidic products of the dehydrogenation, such as prenal.

There are also only a few reports in the prior art on the anaerobic dehydrogenation of primary alcohols using homogeneous catalysts. A homogeneous iridium radical complex for the dehydrogenation of unsaturated alcohols is described by N. Donati et al., Comptes Rendus Chimie 10 (2007) 721-730. In order to keep the catalytic cycle alive, however, 1,4-benzoquinone as a reoxidant is required for regenerating the reactive radical complex in more than stoichiometric amounts in respect to the alcohol. Ruthenium catalyzed homogeneous dehydrogenations of simple saturated alcohols is described in JP 2008-214289, JP 2010-184877 and JP 2004-033798 and by A. Dobson and S. D. Robinson, J. Organomet. Chem. 87 (1975) C52-C53. However, the dehydrogenation of allylic alcohols is either not disclosed in the aforementioned references or, in the latter one, described to result in the decomposition of the desired product. In any case, none of these references report on the preparation of 3-substituted 2-alkenals.

In addition, the oxidation of allylic alcohols to $\alpha,\beta$-unsaturated carbonyl compounds catalyzed by zirconium(IV) complexes in the presence of benzaldehyde as hydrogen acceptor is disclosed by T. Nakano et al., J. Org. Chem. 52 (1987) 4955-4959. It has to be noted that this reference explicitly discourages from using cyclohexanone as hydrogen acceptor for the dehydrogenation of primary allylic alcohols. What is more, the dehydrogenations described require 2 mol-% of the zirconium(IV) catalyst in relation to the molar amount of allylic alcohol used, which is an unacceptably high amount in particular for industrial scale applications.

Moreover, M. Nielsen et al., Angew. Chem. (2011) 9767-9771 disclose a method for an efficient hydrogen production via an acceptorless dehydrogenation of isopropanol or ethanol using a ruthenium(II) catalyst. As hydrogen is the desired product, this process is intended for the conversion of simple alcohols that are relevant renewable hydrogen sources, in particular ethanol. The method described does also not provide means for the continuos removal of the hydrogen from the reaction mixture.

It was an object of the Invention to specify a simple and efficient process for preparing 3-substituted 2-alkenals, in particular prenal that is suitable for industrial scale preparations.

It has now been found that this object is achieved by a liquid phase process that uses Ru(II) or Ir(I) complexes as catalysts for the dehydrogenation of 3-substituted 2-alken-1-ols, such as prenol, and/or 3-substituted 3-alken-1-ols, such as isoprenol.

More specifically the present Invention provides a process for preparing 2-alkenals of the formula I

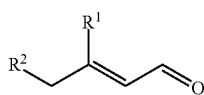

in which
R¹ is selected from hydrogen and $C_1$-$C_4$-alkyl; and
R² is selected from hydrogen, $C_1$-$C_{12}$-alkyl, $C_2$-$C_{12}$-alkenyl, $C_4$-$C_8$-cycloalkyl and $C_6$-$C_{10}$-aryl, wherein $C_1$-$C_{12}$-alkyl and $C_1$-$C_{12}$-alkenyl may be substituted with $C_5$-$C_7$-cycloalkyl or $C_5$-$C_7$-cylcoalkenyl;
comprising dehydrogenating an alkenol of the formula II, an alkenol of the formula III or a mixture thereof,

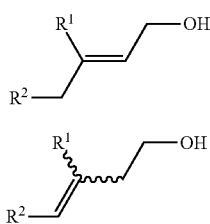

wherein
R¹ and R² are each as defined above,
wherein the alkenol II, the alkenol III or a mixture thereof is brought into contact with a catalytic system comprising at least one ligand and a metal compound selected from ruthenium(II) compounds and iridium(I) compounds, and
wherein the hydrogen formed during the dehydrogenation is removed from the reaction mixture by:
i) reaction with a reoxidant selected from $C_3$-$C_{12}$-alkanones, $C_4$-$C_9$-cycoalkanones, benzaldehyde and mixtures thereof; and/or
ii) purely physical means.

The wavy lines in formula III indicate that the variable R¹ is either positioned cis or trans in relation the variable R². Thus, the alkenol of the formula III may be present as its cis isomer, its trans isomer or a mixture of these isomers.

The process according to the invention is associated with a series of advantages. To begin with, the process according to the invention enables preparation of 3-substituted 2-alkenals of the formula I under mild conditions, in good to very good yields and with high selectivities, while requiring only moderate to low amounts of catalyst, typically in a range clearly below 2 mol-% in relation to the molar amount of alkenol used. Moreover, the inventive process either does not require a reoxidant at all or uses a reoxidant selected from $C_3$-$C_{12}$-alkanones, $C_4$-$C_9$-cycoalkanones, benzaldehyde and mixtures thereof. Consequently, during the reaction no water is formed which would hamper the isolation and purification of the product. It is therefore another advantage of the process of the invention that the obtained 3-substituted 2-alkenals can be easily isolated in high purity.

In the context of the present invention, the terms used generically are defined as follows:

The prefix $C_x$-$C_y$ denotes the number of possible carbon atoms in the particular case.

The term "halogen" denotes in each case fluorine, bromine, chlorine or iodine, especially fluorine, chlorine or bromine.

The term "$C_1$-$C_4$-alkyl" denotes a linear or branched alkyl radical comprising from 1 to 4 carbon atoms, such as methyl, ethyl, propyl, 1-methylethyl(isopropyl), butyl, 1-methylpropyl(sec-butyl), 2-methylpropyl(isobutyl) or 1,1-dimethylethyl(tert-butyl).

The term "$C_1$-$C_{12}$-alkyl" denotes a linear or branched alkyl radical comprising from 1 to 12 carbon atoms. Examples are, as well as the radicals specified for $C_1$-$C_4$-alkyl, pentyl, hexyl, heptyl, octyl, 2-ethylhexyl, nonyl, decyl, undecyl, dodecyl, 2-propylheptyl, 3-butyloctyl and positional isomers thereof.

The term "cycloalkyl" denotes monocyclic saturated hydrocarbon groups having 4 to 8 ($C_4$-$C_8$-cycloalkyl) or 5 to 7 ($C_5$-$C_7$-cycloalkyl) carbon ring members, such as cyclobutyl, cyclopentyl, cyclohexyl, cycloheptyl and cyclooctyl;

The terms "alkylene" and "alkanediyl" are used synonymously and refer to a divalent saturated hydrocarbon radical having a straight or branched chain, which has from 1 to 10 or 3 to 8 carbon atoms, such as propane-1,3-diyl, propane-1,2-diyl, butane-1,4-diyl, butane-1,3-diyl and pentane-1,5-diyl.

The term "cycloalkanediyl" refers to a divalent saturated cyclic hydrocarbon radical, which has from 3 to 9 or 3 to 7 carbon atoms, such as cyclopropane-1,2-diyl, cyclobutane-1,3-diyl, cyclopentane-1,2-diyl, cyclohexane-1,4-diyl, cycloheptane-1,3-diyl.

The term "$C_1$-$C_4$-haloalkyl", as used herein and in the haloalkyl units of $C_1$-$C_4$-haloalkoxy, describes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroisopropyl, 1-chlorobutyl, 2-chlorobutyl, 3-chlorobutyl, 4-chlorobutyl, 1-fluorobutyl, 2-fluorobutyl, 3-fluorobutyl, 4-fluorobutyl and the like.

The term "alkoxy" denotes straight-chain or branched saturated alkyl groups comprising from 1 to 6 ($C_1$-$C_6$-alkoxy) or 1 to 4 ($C_1$-$C_4$-alkoxy) carbon atoms, which are bound via an oxygen atom to the remainder of the molecule, such as methoxy, ethoxy, n-propoxy, 1-methylethoxy(isopropoxy), n-butyloxy, 1-methylpropoxy(sec-butyloxy), 2-methylpropoxy(isobutyloxy) and 1,1-dimethylethoxy(tert-butyloxy).

The term "($C_1$-$C_6$-alkoxy)carbonyl" denotes alkoxy radicals having from 1 to 6 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, sec-butoxycarbonyl, isobutoxycarbonyl and tertbutoxycarbonyl, n-pentyloxycarbonyl and n-hexyloxycarbonyl.

The term "($C_1$-$C_6$-alkylamino)carbonyl" denotes alkylamino radicals having from 1 to 6 carbon atoms which are bound via a carbonyl group to the remainder of the molecule. Examples thereof are methylaminocarbonyl, ethylaminocarbonyl, propylaminocarbonyl, isopropylaminocarbonyl, n-butylaminocarbonyl, sec-butylaminocarbonyl, isobutylaminoylaminocarbonyl and tert-butylaminocarbonyl, n-pentylaminocarbonyl and n-hexylaminocarbonyl.

The term "aryl" denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

The term "arenediyl" refers to divalent aromatic radicals having from 6 to 14 or 6 to 10 carbon atoms, such as benzene-1,2-diyl, benzene-1,3-diyl, benzene-1,4-diyl or naphthalene-1,2-diyl.

The term "heterocyclyl" includes in general 3-, 4-, 5-, 6-, 7- or 8-membered, in particular 5-, 6-, 7- or 8-membered monocyclic heterocyclic non-aromatic radicals and 8 to 10 membered bicyclic heterocyclic non-aromatic radicals, the mono- and bicyclic non-aromatic radicals may be saturated or unsaturated. The mono- and bicyclic heterocyclic non-aromatic radicals usually comprise 1, 2, 3 or 4 heteroatoms selected from N, O and S as ring members, where S-atoms as ring members may be present as S, SO or $SO_2$. Examples of saturated or unsaturated 3-, 4-, 5-, 6-, 7- or 8-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, S-oxothiolanyl, S-dioxothiolanyl, dihydrothienyl, S-oxodihydrothienyl, S-dioxodihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "heterocyclene" refers to divalent heterocyclic radicals which correspond to the heterocyclyl radicals, as defined above, having an additional site of attachment.

The term "hetaryl" denotes aromatic radicals having from 1 to 4 heteroatoms which are selected from O, N and S. Examples thereof are 5- and 6-membered hetaryl radicals having 1, 2, 3 or 4 heteroatoms selected from O, S and N, such as pyrrolyl, furanyl, thienyl, pyrazolyl, imidazolyl, oxazolyl, isoxazolyl, thiazolyl, isothiazolyl, triazolyl, tetrazolyl, pyridyl, pyrazinyl, pyridazinyl, pyrimidyl and triazinyl.

The term "hetarenediyl" refers to divalent hetaromatic radicals which correspond to the hetaryl radicals, as defined above, having an additional site of attachment.

The term "aryl-$C_1$-$C_6$-alkyl" denotes aryl radicals which are bound via a $C_1$-$C_6$-alkyl group to the remainder of the molecule. Examples thereof are benzyl, 2-phenylethyl(phenethyl) and the like.

The term "reoxidant" refers to a compound other than the catalytic system or a compound of formulae I, II or III that is able to bind hydrogen via a chemical bond. The hydrogen acceptor most commonly used in the prior art for this purpose is oxygen which binds hydrogen generated in the dehydrogenation step by oxidizing it to water. The only reoxidants included in the process of the present invention are selected from $C_3$-$C_{12}$-alkanone, $C_4$-$C_9$-cycoalkanone and benzaldehyde and are exclusively used in the optional step i) of the inventive process.

The remarks made below regarding preferred embodiments of the process according to the invention, especially regarding preferred meanings of the variables of the different reactants and products and of the reaction conditions of the process, apply either taken alone or, more particularly, in any conceivable combination with one another.

In the compounds of the formulae I, II and III $R^1$ is preferably hydrogen or $C_1$-$C_2$-alkyl, more preferably methyl or ethyl and in particular is methyl.

In the compounds of the formulae I, II and III $R^2$ is preferably hydrogen, $C_1$-$C_8$-alkyl, $C_2$-$C_8$-alkenyl, $C_4$-$C_8$-cycloalkyl or phenyl, more preferably hydrogen, $C_1$-$C_8$-alkyl or $C_2$-$C_8$-alkenyl, even more preferably hydrogen or $C_2$-$C_8$-alkenyl, in particular hydrogen or 3-methyl-2-buten-1-yl and specifically hydrogen.

In the compounds of the formula III the substituent $R^1$ is either in the trans- or in the cis-position and preferably is in the cis-position related to the substituent $R^2$.

According to a preferred embodiment of the present invention $R^1$ is methyl and $R^2$ is hydrogen or 3-methyl-2-buten-1-yl and in particular hydrogen.

The inventive conversions described hereinafter are performed in reaction vessels customary for such reactions, the reaction being configurable in a continuous, semicontinuous or batchwise manner. In general, the particular reactions will be performed under atmospheric pressure. The conversions may, however, also be performed under reduced or increased pressure. As described in detail below, it may be advantageous to carry out the dehydrogenation of the inventive process under reduced pressure if it is effected pursuant to step ii), or at increased pressure if it is effected pursuant step i). The conversion of the process according to the invention for preparing 2-alkenals I is a dehydrogenation reaction leading to the formation of a carbonyl group conjugated with a double bond. The reaction is carried out by contacting the starting compounds, i.e. an alkenol of the formula II and/or an alkenol of the formula III, a catalytic system and, if applicable, a reoxidant, optionally in a solvent, under suitable reaction conditions.

In general, the dehydrogenation is performed under temperature control. The reaction is typically effected in an unclosed or closed reaction vessel with stirring and heating apparatus.

The starting compounds can in principle be contacted with one another in any desired sequence. For example, an alkenol of formula II and/or an alkenol of formula III, if appropriate dissolved in a solvent or in dispersed form, can be initially charged and admixed with the catalytic system or, conversely, the catalytic system, if appropriate dissolved in a solvent or in dispersed form, can be initially charged and admixed with an alkenol of formula II and/or an alkenol of formula III. Alternatively, these two components can also be added simultaneously to the reaction vessel. In case dehydrogenation of both, an alkenol II and also an alkenol III, is intended, the two alkanols can, independently of each other, be added before or after the addition of the catalytic system or else together with it, either in a solvent or in bulk. Likewise, in case the dehydrogenation is effected according to step i) the reoxidant can be added before or after the addition of the catalytic system or else together with it, either in a solvent or in bulk. If employed at all the reoxidant is preferably added not after both the catalytic system and alkenol II and/or alkenol III have been charged to the reaction vessel. Moreover, as an alternative to their joint addition the two components of the catalytic system, the ligands and the metal compound, can be added separately to the reaction vessel. Both of them can independently of one another be added before or after the addition of one of the reactants or else together with one of the reactants.

The dehydrogenation of the inventive process may be carried out in the presence or in the absence of a solvent. In the latter case the reactant, i.e. the alkenol II and/or III, may be used as a solvent. Furthermore, in case the dehydrogenation is performed according to step i), the reoxidant may not only bind the hydrogen formed during the reaction but also function as solvent. For example, if prenol is employed as alkenol II it can suitably also serve as solvent and a reoxidant, for example 3-pentanone, may serve as additional solvent if the dehydrogenation is carried out via step i). In such cases the addition of a designated solvent is not compulsory. However, if the dehydrogenation is performed according to step ii), preference is given to carry out the reaction in the presence of a designated solvent, whereas the conversions via step i) are preferable effected without using a liquid having the sole purpose of being a solvent.

It has been found to be appropriate to initially establish inert conditions, in particular by exchanging the atmosphere to nitrogen or argon, and then charge the reaction vessel with an alkenol of formula II and/or an alkenol of formula III, a reoxidant, if appropriate, and a metal compound and one or more ligands either jointly or successively. In case a specific solvent is used, it is added preferably only after inert conditions have been established.

Suitable solvents depend in the individual case on the selection of the particular starting compounds and reaction conditions. It has generally been found to be advantageous to use an aprotic organic solvent for the reaction of the alkenols of formula II and/or formula III. Useful aprotic organic solvents here include, for example, aliphatic hydrocarbons, such as hexane, heptane, octane, nonane, decane and also petroleum ether, aromatic hydrocarbons, such as benzene, toluene, the xylenes and mesitylene, aliphatic $C_3$-$C_8$-ethers, such as 1,2-dimethoxyethane (DME), diethylene glycol dimethyl ether (diglyme), diethyl ether, dipropyl ether, methyl isobutyl ether, tert-butyl methyl ether and tert-butyl ethyl ether, cycloaliphatic hydrocarbons, such as cyclohexane and cycloheptane, alicyclic $C_3$-$C_6$-ethers, such as tetrahydrofuran (THF), tetrahydropyran, 2-methyltetrahydrofuran, 3-methyltetrahydrofuran and 1,4-dioxane, short-chain ketones, such as ethyl methyl ketone and isobutyl methyl ketone, amides such as dimethylformamide (DMF), dimethylacetamide and N-methylpyrrolidone (NMP), dimethyl sulfoxide (DMSO), acetonitrile, or mixtures of these solvents with one another.

According to an embodiment of the present invention those of the aforementioned aprotic solvents are preferred that have a boiling point above 50° C., for instance in the range of 50 to 200° C., in particular above 65° C., for instance in the range of 65 to 180° C., and specifically above 80° C., for instance in the range of 80 to 160° C.

More preferably the solvent, if employed, is selected from toluene, the xylenes, mesitylene, $C_7$-$C_{10}$-alkanes, such as octane or nonane, THF, 1,4-dioxane and mixtures thereof, and specifically selected from toluene, ortho-xylene, meta-xylene, para-xylene, mesitylene and mixtures thereof.

If the catalytic system includes a ruthenium(II) compound, the solvent for the dehydrogenation is preferably selected from toluene, ortho-xylene, meta-xylene, para-xylene, mesitylene and mixtures thereof, and more preferably from toluene, ortho-xylene, meta-xylene, para-xylene and mixtures thereof. In this context toluene is particularly preferred.

If the catalytic system includes a iridium(I) compound, the solvent for the dehydrogenation is preferably selected from THF, 1,4-dioxane, toluene, ortho-xylene, meta-xylene, para-xylene, mesitylene and mixtures thereof, and more preferably from toluene, ortho-xylene, meta-xylene, para-xylene, mesitylene and mixtures thereof. In this context toluene, ortho-xylene, meta-xylene, para-xylene and mixtures thereof are particularly preferred.

If employed the solvent is used in the dehydrogenation of the process according to the invention in a total amount that is typically in the range from 100 to 20000 g and preferably in the range from 100 to 1500 g, based on 1 mol of the alkenol II and/or III.

Preference is given to using solvents which are essentially anhydrous, i.e. have a water content of less than 1000 ppm and especially not more than 100 ppm.

2-Alken-1-ols of the formula II and 3-alken-1-ols of the formula III are commercially available or can be prepared by customary processes. 2-Alken-1-ols II are obtainable, for instance, by alkaline hydrolysis of the corresponding allylic halide or by catalytic isomerisation of the corresponding 1,2-epoxyalkane, in accordance to established procedures. 3-Alken-1-ols III are obtainable, for instance, by an electrophilic addition of formaldehyde to a respective alkene followed by partial dehydration, according to well-known methods. In a subsequent step the obtained 3-alken-1-ol III can be catalytically isomerized to the corresponding 2-alken-1-ol II. The latter approach is, for example, an important route for the industrial production of isoprenol and prenol.

For the dehydrogenation of the process according to the invention alkenols of the formula II, alkanols of the formula III or mixtures thereof may be employed. If a mixture of alkenols of the formulae II and III is subjected to the dehydrogenation of the present invention, the mixture preferably consists of one alkenol II and one alkanol III which both have identical substituents $R^1$ and $R^2$. However, it is particularly preferred that either one alkenol II or one alkanol III is exclusively subjected to the inventive dehydrogenation.

According to an embodiment of the invention those alkenols of the formula II and those alkanols of the formula III are employed in the inventive processes in which the variable $R^1$ represents hydrogen or $C_1$-$C_2$-alkyl and in particular methyl, and the variables $R^2$ represents hydrogen, $C_1$-$C_6$-alkyl or $C_2$-$C_6$-alkenyl. Particular suitable alkanols of the formula III are additionally characterized in that the substituent $R^1$ is in the cis-position related to the substituent $R^2$.

According to a preferred embodiment of the invention only one alkenol of the formula II is subjected to dehydrogenation of the inventive process, wherein the one alkenol II is preferably selected from prenol (3-methyl-2-buten-1-ol) and geraniol ((E)-3,7-dimethyl-2,6-octadien-1-ol) and in particular is prenol.

According to another preferred embodiment of the invention only one alkenol of the formula III is subjected to the dehydrogenation of the inventive process, wherein the one alkenol III is preferably selected from isoprenol (3-methyl-3-buten-1-ol) and isogeraniol ((Z)-3,7-dimethyl-3,6-octadien-1-ol) and in particular is isoprenol.

As already mentioned above, the hydrogen formed during the dehydrogenation of the process of the invention is removed from the reaction mixture by one of the following steps or a combination thereof:
i) reaction with a reoxidant selected from $C_3$-$C_{12}$-alkanones, $C_4$-$C_9$-cycoalkanones, benzaldehyde and mixtures thereof;
ii) purely physical means.

The dehydrogenations the inventive process that are performed pursuant to step i) are herein also referred to as transfer-dehydrogenations, and those performed pursuant to step ii) are herein also referred to as reoxidant-free dehydrogenations.

The hydrogen that is formed as a by-product of the dehydrogenation is usually required to be removed during the process of the invention in order to avoid undesired hydrogenations that may occur as side-reactions if hydrogen is present. In addition, via removal of the hydrogen it is often possible to shift the equilibrium of the dehydrogenation toward the desired 2-alkenal of formula I.

In this context of this invention the term "physical means" encompasses all physical methods known in the art that are suitable for removing a hydrogen from a liquid. Said physical means for removing hydrogen are preferably selected from the methods for expelling the hydrogen by boiling the reaction mixture, by reducing the atmospheric pressure within the reaction vessel, by passing an auxiliary gas through the reaction mixture and by combinations of these methods.

According to a preferred embodiment of the invention the hydrogen formed during the dehydrogenation of the inventive process is solely removed pursuant to step ii), i.e. by purely physical means, wherein the physical means preferably consist of expelling the hydrogen by boiling the reaction mixture and/or passing an auxiliary gas through the reaction mixture and in particular consist of expelling the hydrogen by boiling the reaction mixture.

According to a another preferred embodiment of the invention the hydrogen formed during the dehydrogenation of the inventive process is solely removed pursuant to step i), i.e. by reaction with a reoxidant that is generally selected from $C_3$-$C_{12}$-alkanones, $C_4$-$C_9$-cycoalkanones, benzaldehyde and mixtures thereof, preferably selected from $C_3$-$C_6$-alkanones, $C_5$-$C_7$-cycoalkanones and benzaldehyde, and in particular selected from acetone, 3-pentanone, cyclohexanone and benzaldehyde.

If an alkenol of the formula II is subjected to the inventive process, the hydrogen is preferably removed pursuant to step ii), i.e. by purely physical means.

If an alkenol of the formula III is subjected to the inventive process, the hydrogen is preferably removed pursuant to step i), i.e. by reaction with a reoxidant selected from $C_3$-$C_{12}$-alkanones, $C_4$-$C_9$-cycoalkanones, benzaldehyde and mixtures thereof.

Suitable catalytic systems for the dehydrogenation of the process according to the invention are metal complexes comprising at least one complex ligand, wherein the metal compound is preferably selected from
a) ruthenium compounds in which ruthenium has an oxidation state of 0, 2 or 3, and
b) iridium compounds in which iridium has an oxidation state 0, 1 or 3.

If ruthenium compounds in which ruthenium has an oxidation state of 0 or 3 are used they have to be transformed, either before or during the dehydrogenation of the inventive process, into ruthenium compounds with ruthenium being in the oxidation state 2. Likewise, if iridium compounds in which iridium has an oxidation state of 0 or 3 are used they have to be transformed, either before or during the dehydrogenation of the inventive process, into iridium compounds with iridium being in the oxidation state 1.

The catalytic system of the process of the invention can be employed in the form of a preformed metal complex which comprises the metal compound and one or more ligands. Alternatively, the catalytic system is formed in situ in the reaction mixture by combining a metal compound, herein also termed pre-catalyst, with one or more suitable ligands to form a catalytically active metal complex in the reaction mixture.

Suitable pre-catalysts are selected from neutral metal complexes, oxides and salts of ruthenium or iridium. Ruthenium compounds that are useful as pre-catalyst are, for example, [Ru(p-cymene)Cl$_2$]$_2$, [Ru(benzene)Cl$_2$]$_n$, [Ru(CO)$_2$Cl$_2$]$_n$, [Ru(CO)$_3$Cl$_2$]$_2$, [Ru(COD)(allyl)], [RuCl$_3$.H$_2$O], [Ru(acetylacetonate)$_3$], [Ru(DMSO)$_4$Cl$_2$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$], [Ru(Cp)(PPh$_3$)$_2$Cl], [Ru(Cp)(CO)$_2$Cl], [Ru(Cp)(CO)$_2$H], [Ru(Cp)(CO)$_2$]$_2$, [Ru(Cp*)(CO)$_2$Cl], [Ru(Cp*)(CO)$_2$H], [Ru(Cp*)(CO)$_2$]$_2$, [Ru(indenyl)(CO)$_2$Cl], [Ru(indenyl)(CO)$_2$H], [Ru(indenyl)(CO)$_2$]$_2$, ruthenocen, [Ru(binap)(Cl)$_2$], [Ru(2,2'-bipyridin)$_2$(Cl)$_2$.H$_2$O], [Ru(COD)(Cl)$_2$H]$_2$, [Ru(Cp*)(COD)Cl], [Ru$_3$(CO)$_{12}$], [Ru(tetraphenylhydroxycyclopentadienyl)(CO)$_2$H], [Ru(PMe$_3$)$_4$(H)$_2$], [Ru(PEt$_3$)$_4$(H)$_2$], [Ru(Pn-Pr$_3$)$_4$(H)$_2$], [Ru(Pn-Bu$_3$)$_4$(H)$_2$], [Ru(Pn-octyl$_3$)$_4$(H)$_2$], of which Ru(COD)Cl$_2$]$_2$, [Ru(Pn-Bu$_3$)$_4$(H)$_2$], [Ru(Pn-octyl$_3$)$_4$(H)$_2$], [Ru(PPh$_3$)$_3$(CO)(H)Cl] and [Ru(PPh$_3$)$_3$(CO)(H)$_2$] are preferred. Iridium compounds that are useful as pre-catalyst are, for example, [IrCl$_3$.H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(Cp)Cl$_2$]$_2$, [Ir(Cp*)Cl$_2$]$_2$, [Ir(Cp)(CO)$_2$], [Ir(Cp*)(CO)$_2$], [Ir(PPh$_3$)$_2$(CO)Cl] and [Ir(PPh$_3$)$_3$Cl], of which [Ir(COD)Cl]$_2$, [Ir(cyclooctene)$_2$Cl]$_2$ and [Ir(Cp*)Cl$_2$]$_2$ are preferred. In the aforementioned compound names "COD" denotes 1,5-cyclooctadiene; "Cp" denotes cyclopentadienyl; "Cp*" denotes pentamethylcyclopentadienyl; and "binap" denotes 2,2'-bis(diphenylphosphino)-1,1'-binaphthyl.

For the dehydrogenation of the process according to the present invention any complex ligands known in the art, in particular those known to be useful in catalytic ruthenium and iridium complexes, may be employed.

Suitable ligands of the catalytic system for the dehydrogenation of the process according to the invention are, for example, mono-, bi- and tridentate phosphines of the formulae IV, V and VI shown below,

(IV)

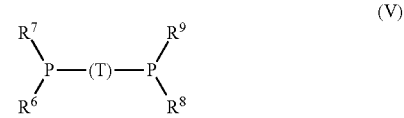
(V)

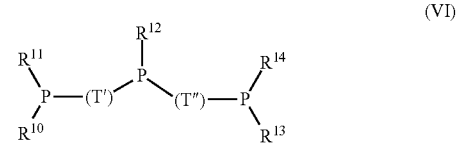
(VI)

in which $R^3$ to $R^{14}$ are each independently selected from $C_1$-$C_{12}$-alkyl, adamantyl, ferrocenyl, aryl and aryl-$C_1$-$C_3$-alkyl, $C_3$-$C_{12}$-cycloalkyl, $C_5$-$C_8$-cycloalkyl-$C_1$-$C_3$-alkyl, where cycloalkyl in the two last-mentioned radicals may be mono- or bicyclic and where cycloalkyl and aryl in the four last-mentioned radicals may optionally carry one or more substituents selected from $C_1$-$C_4$-alkyl, $C_1$-$C_4$-alkoxy, fluorine and chlorine, or
one or more pairs of moieties selected from $R^6$, $R^7$, $R^8$, and $R^9$ or selected from $R^{10}$, $R^{11}$, $R^{12}$, $R^{13}$ and $R^{14}$ may optionally form a $C_3$-$C_8$-alkanediyl bridge which optionally is substituted by 1, 2 or 3 substituents selected from $C_1$-$C_4$-alkyl or $C_3$-$C_6$-cycloalkyl and is optionally part of one or two mono- or bicyclic rings, and
T, T' and T" are each independently selected from $C_1$-$C_6$-alkanediyl, $C_0$-$C_1$-alkyleneferrocenyl, 1,1'-biphenyl-2,2'-diyl and 1,1'-binaphthyl-2,2'-diyl, where the latter four radicals may optionally be substituted by $C_1$-$C_6$-alkyl or $C_1$-$C_4$-alkoxy, and where $C_1$-$C_6$-alkanediyl may have one or more substituents selected from $C_1$-$C_{10}$-alkyl, $C_3$-$C_7$-cycloalkyl, aryl and benzyl. Also, the $C_1$-$C_6$-alkanediyl may optionally be part of one or two mono- or bicyclic rings which are unsubstituted or substituted. The $C_0$-$C_1$-alkyleneferrocenyl mentioned above is preferably selected from ferrocenediyl, where the two phosphorus atoms are bound to the same or different cyclopentadienes of the ferrocene, or methyleneferrocenyl, where one of the phosphorus atoms is bound via the methylene group to a cyclopentadiene, the second phosphorus atom is bound directly to the same cyclopentadiene, and the methylene group may optionally have 1 or 2 further substituents selected from $C_1$-$C_4$-alkyl.

Preferably, the variables $R^3$ to $R^{14}$ in the compounds of the formulae IV, V and VI are each independently selected from $C_1$-$C_{12}$-alkyl, adamantyl, ferrocenyl, aryl, aryl-$C_1$-$C_2$-alkyl and $C_3$-$C_{12}$-cycloalkyl which may be mono- or bicyclic, where cycloalkyl and aryl in the three last-mentioned radicals may optionally carry one or more substituents selected from $C_1$-$C_4$-alkyl, $C_1$-$C_4$-alkoxy, fluorine and chlorine. More preferably the variables $R^6$ to $R^{17}$ are each independently selected from $C_1$-$C_{12}$-alkyl, phenyl, phenyl-$C_1$-$C_2$-alkyl and $C_5$-$C_9$-cycloalkyl which may be mono- or bicyclic, where cycloalkyl and phenyl in the three last-mentioned radicals may optionally carry 1 or 2 substituents selected from $C_1$-$C_4$-alkyl. Preferred variables $R^6$ to $R^{17}$ are independently of each other specifically selected from methyl, ethyl, 1-propyl, 2-propyl, 1-butyl, 2-butyl, 2-methyl-1-propyl, 2-methyl-2-propyl, 1-pentyl, 1-hexyl, 1-heptyl, 1-octyl, 1-nonyl, 1-decyl, 1-undecyl, 1-docecyl, cyclopentyl, cyclohexyl, cycloheptyl, cyclooctyl, methylcyclopentyl, methylcyclohexyl, 2-methyl-1-pentyl, 2-ethyl-2-hexyl, 2-propyl-1-heptyl, phenyl, tolyl, xylyl and norbornyl.

Particularly preferred variables $R^3$ to $R^{14}$ are each Independently selected from $C_1$-$C_{10}$-alkyl and $C_4$-$C_8$-cycloalkyl, and specifically from ethyl, 1-butyl, sec-butyl, 1-octyl and cyclohexyl.

Preferably, the variables T, T' and T" in the compounds of the formulae V and VI are each independently selected from $C_1$-$C_5$-alkanediyl which may optionally carry one or more substituent selected form $C_1$-$C_8$-alkyl, $C_3$-$C_6$-cycloalkyl, phenyl and benzyl. In addition the $C_1$-$C_5$-alkanediyl radical may optionally be part of one or two mono- or bicyclic rings which are unsubstituted or substituted.

Particularly preferred variables T, T' and T" are each independently selected from $C_1$-$C_4$-alkylene which may optionally carry one substituent selected form $C_1$-$C_4$-alkyl, $C_3$-$C_7$-cycloalkyl, phenyl and benzyl, and may also be part of one or two $C_3$-$C_7$-cycloalkyl rings which are unsubstituted or carry 1 or 2 substituents selected from $C_1$-$C_4$-alkyl, $C_1$-$C_4$-alkoxy, fluorine and chlorine. Specifically T, T' and T" are each independently selected from methanediyl, ethane-1,2-diyl, propane-1,3-diyl, propane-1,2-diyl, 1,4-butanediyl and 1,3-butanediyl.

Monodentate ligands of the formula IV preferred herein are those in which $R^3$, $R^4$ and $R^5$ are each phenyl optionally carrying 1 or 2 $C_1$-$C_4$-alkyl substituents and those in which $R^6$, $R^7$ and $R^8$ are each $C_5$-$C_8$-cycloalkyl or $C_2$-$C_{10}$-alkyl, in particular linear unbranched n-$C_2$-$C_{10}$-alkyl. The groups $R^3$ to $R^5$ may be different or identical. Preferably the groups $R^3$ to $R^5$ are identical and are selected from the substituents mentioned herein, in particular from those indicated as preferred. Examples of preferable monodentate ligands IV are triphenylphosphine (TPP), triethylphosphine, tri-n-butylphosphine, tri-n-octylphosphine and tricyclohexylphosphine.

Bidentate ligands of the formula V preferred herein are those in which T is $C_1$-$C_4$-alkylene and $R^6$, $R^7$, $R^8$ and $R^9$ are either each selected from phenyl optionally carrying 1 or 2 $C_1$-$C_4$-alkyl substituents or are each selected from $C_5$-$C_8$-cycloalkyl and $C_2$-$C_{10}$-alkyl, in particular linear unbranched n-$C_2$-$C_{10}$-alkyl. The groups $R^6$ to $R^9$ may be different or identical. Preferably the groups $R^6$ to $R^9$ are identical and are selected from the substituents mentioned herein, in particular from those indicated as preferred. Examples of preferable bidentate ligands V are 1,2-bis(diphenylphosphino)ethane, 1,2-bis(dicyclohexylphosphino)methane, 1,2-bis(dicyclohexylphosphino)ethane and 1,2-bis(dicyclohexylphosphino)propane.

Further suitable ligands of the catalytic system for the dehydrogenation of the process according to the invention are N-heterocyclic carbenes, known as NHC ligands. Herein preferred NHC ligands are those of the formulae VII and VIII shown below,

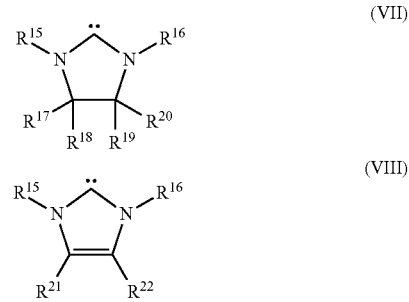

in which $R^{15}$ and $R^{16}$ are each independently selected from $C_1$-$C_{10}$-alkyl, aryl and hetaryl, where aryl and hetaryl may optionally carry 1, 2, 3 or 4 substituents selected from $C_1$-$C_8$-alkyl and $C_3$-$C_7$-cycloalkyl, $R^{17}$, $R^{18}$, $R^{19}$ and $R^{20}$ are each independently selected from hydrogen, $C_1$-$C_8$-alkyl and aryl, or two of the radicals $R^{17}$, $R^{18}$, $R^{19}$ and $R^{20}$ form a saturated five- to seven-membered ring, where the two other radicals are each independently hydrogen or methyl, and $R^{21}$ and $R^{22}$ are each independently selected from hydrogen, $C_1$-$C_8$-alkyl and aryl, or $R^{21}$ and $R^{22}$, together with the heterocyclic moiety to which they are bonded, are a fused ring system with 1 or 2 aromatic rings.

Preferably, the variables $R^{15}$ and $R^{16}$ in the compounds of the formulae VII and VIII independently of each other are $C_1$-$C_{10}$-alkyl or phenyl that optionally carries 1 or 2 substituents selected from $C_1$-$C_8$-alkyl. Particular preferred variables $R^{15}$ and $R^{16}$ are independently selected from $C_1$-$C_8$-alkyl. $R^{15}$ and $R^{16}$ may be identical or different and are preferably different from each other.

Preferably, the variables $R^{17}$, $R^{18}$, $R^{19}$ and $R^{20}$ in the compounds of the formula VII are each independently selected from hydrogen, $C_1$-$C_8$-alkyl and aryl, more preferably hydrogen and $C_1$-$C_6$-alkyl, and specifically are all hydrogen.

Preferably, the variables $R^{21}$ and $R^{22}$ in the compounds of the formula VIII are each independently selected from hydrogen, $C_1$-$C_8$-alkyl and phenyl, and specifically are both hydrogen.

NHC ligands preferred herein are those of formula VIII in which $R^{15}$, $R^{16}$, $R^{21}$ and $R^{22}$ have the meanings given herein, in particular the meanings mentioned as preferred.

NHC ligands of formula VIII can be obtained in situ from imidazolium salts, for example 1-methyl-3-butyl-4,5-H2-imidazolium chloride, with bases, and be converted to suitable catalysts in the presence of metal compounds such as ruthenium(II) or iridium(I) compounds. However, it is also possible to prepare NHC complex salts of metal compounds beforehand, e.g. [Ru(NHC)$_4$Cl$_2$], [Ru(NHC)(p-cymene)Cl$_2$], [Ru(NHC)(NCMe)$_2$]Cl$_2$, [Ru(NHC)$_4$(H)]Cl, [Ru(NHC)$_4$(H)][BEt$_4$], [Ru(NHC)$_4$(H)$_2$], [Ru(NHC)$_2$(CO)HCl], [Ru(NHC)$_2$(CO)$_2$HCl], [Ru(NHC)(PPh$_3$)(CO)HCl], [Ru(NHC)(PPh$_3$)(CO)$_2$HCl], [Ru(NHC)(PMe$_2$Ph)$_2$(CO)H$_2$], [Ru(NHC)$_2$(CO)$_2$H$_2$], [Ru(NHC)$_2$(CO)$_3$], [Ru$_3$(CO)$_{11}$(NHC)], [Ru(NHC)$_2$(CO)$_2$(CO$_3$)], [Ru(NHC)(PPh$_3$)$_2$(CO)H], [Ru(NHC)(PPh$_3$)$_2$(CO)H$_2$], [Ru(NHC)$_2$(PPh$_3$)(CO)H$_2$], [Ru(NHC)(PPh$_3$)$_2$(CO)HCl], [Ru(Cp)(NHC)$_2$(Cl)], [Ru(Cp)(NHC)(CO)Cl], [Ru(Cp*)(NHC)$_2$(Cl)], [Ru(Cp*)(NHC)(CO)Cl], [Ru(Cp*)(NHC)(PR$_3$)Cl] and [Ru(Cp)(NHC)(PR$_3$)Cl], to isolate them, and then to use them as preformed catalysts in the dehydrogenation of the invention. In the aforementioned compound names "NHC" denotes a NHC ligand of the formulae VII or VIII, wherein the variables R$^{15}$, R$^{16}$, R$^{17}$, R$^{18}$, R$^{19}$, R$^{20}$, R$^{21}$ and R$^{22}$ have the aforementioned meanings and preferably the meanings mentioned as preferred; "Cp" denotes cyclopentadienyl; "Cp*" denotes pentamethylcyclopentadienyl; and "NCMe" denotes acetonitrile. The aforementioned complexes that include NHC ligands can be prepared for example according to the procedures described in M. Würtemberger, T. Ott, C. Döring, T. Schaub, U. Radius, Eur. J. Inorg. Chem. (2011) 405-415; R. Wolf, M. Plois, A. Hepp, Eur. J. Inorg. Chem. (2010) 918-925; V. L. Chantler, S. L. Chatwin, R. F. R. Jazzar, M. F. Mahon, O. Saker, M. K. Whittlesey, Dalton Trans. (2008) 2603-2614; C. E. Ellul, O. Saker, M. F. Mahon, D. C. Apperley, M. K. Whittlesey, Organometallics 46 (2008) 6343-6345; S. Burling, G. Kociok-Köhn, M. F. Mahon, M. K. Whittlesey, J. M. J. Williams, Organometallics 24 (2005) 5868-5878; and W. Baratta, E. Herdtweck, W. A. Herrmann, P. Rigo, J. Schwarz, Organometallics 21 (2002) 2101-2106.

In general the bases used to convert imidazolium salts to the corresponding NHC ligands of formula VIII are selected from bases commonly known to be useful for similar reactions, such as tri-alkali metal phosphates, e.g. trisodium phosphate and tripotassium phosphate, alkali metal carbonates, e.g. sodium carbonate and potassium carbonate, bicarbonates, such as potassium bicarbonate or sodium bicarbonate, organic bases, such as amines, e.g. triethylamine, pyridine or N,N-diethyl-aniline, and alkali metal alkanolates, e.g. sodium isopropylate and potassium tert-butylate, In this context preferred bases are potassium tert-butylate, tripotassium phosphate and potassium carbonate.

Further suitable ligands of the catalytic system for the dehydrogenation of the process according to the invention are the tridentate ligands of formulae IX and X,

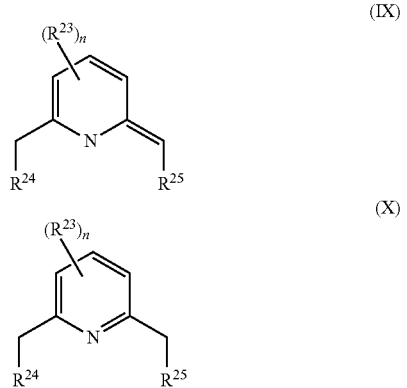

in which
R$^{23}$ is selected from the group consisting of halogen, NO$_2$, CN, C$_1$-C$_{10}$-alkyl, C$_3$-C$_9$-cycloalkyl, aryl, hetaryl, C$_3$-C$_8$-heterocyclyl, C$_1$-C$_{10}$-alkoxy, (C$_1$-C$_6$-alkoxy)carbonyl, (C$_1$-C$_6$-alkylamino)carbonyl, aryl-(C$_1$-C$_6$)-alkyl, an optionally spacer-modified inorganic support, such as e.g. silica, and an optionally spacer-modified organic support, such as a polymeric moiety like polystyrene;
n is 0, 1, 2 or 3;
R$^{24}$ and R$^{25}$ are each independently selected from the group consisting of —PR$_2$, —P(OR)$_2$, —NR$_2$, —NHR, —NH$_2$, =NR, —SR, —SH, —S(=O)R, hetaryl, —AsR$_2$, —SbR$_2$, a carbene of the formula: CRR', and a carbene of the formula

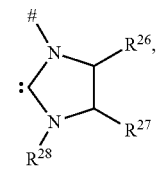

wherein
R, R$^{26}$, R$^{27}$ and R$^{28}$ are independently of each other selected from the group consisting of C$_1$-C$_{10}$-alkyl, C$_3$-C$_9$-cycloalkyl, aryl, aryl-(C$_1$-C$_6$)-alkyl, C$_3$-C$_8$-heterocyclyl and hetaryl, R' is selected from the group consisting of C$_1$-C$_{10}$-alkanediyl, C$_3$-C$_9$-cycloalkanediyl, arenediyl, aryl-(C$_1$-C$_6$)-alkanediyl, C$_3$-C$_8$-heterocyclene and hetarenediyl, and
# is the attachment point to the remainder of the molecule.

Preferably, the aforementioned variables R, R$^{26}$, R$^{27}$ and R$^{28}$ are independently of each other selected from the group consisting of C$_1$-C$_8$-alkyl, C$_3$-C$_8$-cycloalkyl, aryl and aryl (C$_1$-C$_3$)-alkyl, and in particular form C$_1$-C$_6$-alkyl, C$_3$-C$_7$-cycloalkyl, phenyl and benzyl.

Preferably, the aforementioned variable R' is selected from the group consisting of C$_1$-C$_8$-alkanediyl, C$_3$-C$_8$-cycloalkanediyl, arenediyl, aryl-(C$_1$-C$_3$)-alkanediyl, and in particular form C$_1$-C$_6$-alkanediyl, C$_3$-C$_7$-cycloalkanediyl and benzenediyl.

If present, the variable R$^{23}$ in the compounds of the formulae IX and X is preferably selected from the group consisting of halogen, NO$_2$, CN, C$_1$-C$_8$-alkyl, C$_3$-C$_7$-cycloalkyl, aryl, hetaryl, C$_3$-C$_7$-heterocyclyl and C$_1$-C$_8$-alkoxy, and in particular from chlorine, fluorine, NO$_2$, CN, C$_1$-C$_6$-alkyl and C$_1$-C$_6$-alkoxy.

The variable n in the compounds of the formulae IX and X is preferably 0 or 1 and in particular 0.

Preferably, the variables R$^{24}$ and R$^{25}$ in the compounds of the formulae IX and X are each independently selected from the group consisting of —PR$_2$, —P(OR)$_2$, —NR$_2$, —NHR, —NH$_2$, =NR, —SR, —SH, —S(=O)R and hetaryl, and more preferably from —PR$_2$, —P(OR)$_2$, —NR$_2$, —NHR and —NH$_2$, wherein the variable R in each case has one of the aforementioned meanings and in particular one of those meanings Indicated as preferred. In particular, R$^{24}$ and R$^{25}$ are each independently selected from the group consisting of —P(C$_1$-C$_6$-alkyl)$_2$, and specifically are both —P(tert-butyl)$_2$.

In addition to the one or more ligands selected from the groups of ligands described above the catalytic system of the inventive process may also include at least one further ligand which is selected from halides, amides, carboxylates, acetylacetonate, aryl- or alkylsufonates, hydride, CO, olefins, dienes, cycloolefines, nitriles, aromatics and heteroaromatics, ethers, $PF_3$, phospholes, phosphabenzenes, and mono-, di- and polydentate phosphinite, phosphonite, phosphoramidite and phosphite ligands.

According to an embodiment of the present invention, the dehydrogenation is carried out using a catalytic system comprising at least one ligand selected from the herein described monodentate, bidentate and tridentate phosphine ligands, and preferably selected from monodentate and bidentate phosphine ligands of formulae IV and V, in particular from those ligands IV and V mentioned herein as preferred.

According to a preferred embodiment of the invention the catalytic system comprises one to four, preferably one or four ligands selected from monodentate phosphine ligands of formula IV, in particular from those ligands IV mentioned herein as preferred.

According to another preferred embodiment of the invention the catalytic system comprises one to four, preferably two ligands selected from monodentate phosphine ligands of formula IV, in particular from those ligands IV mentioned herein as preferred, and in addition one ligand selected from bidentate phosphine ligands of formula V, in particular from those ligands V mentioned herein as preferred.

According to a further embodiment of the present invention the dehydrogenation is carried out using a catalytic system comprising at least one ligand selected from the herein described NHC ligands and preferably selected from NHC ligands of formulae VII and VIII, in particular from those ligands VII and VIII mentioned herein as preferred.

According to a further preferred embodiment of the invention the catalytic system comprises one to four, preferably two ligands selected from monodentate phosphine ligands of formula IV, in particular from those ligands IV mentioned herein as preferred, and in addition one to four, preferably two ligands selected from NHC ligands of formula VIII, in particular from those ligands VIII mentioned herein as preferred.

Said catalytic systems of the invention that comprise an NHC ligand, in particular those catalytic systems that are based on a ruthenium compound, may also bear at least one co-ligand other than a monodentate phosphine ligand IV, which is selected from olefins, dienes, cycloolefines and arenes, preferably selected from dienes and arenes, and in particular is COD, p-cymene, benzene or hexamethylbenzene.

The aforementioned catalytic systems of the invention comprising at least one of the herein described phosphine ligands and/or at least one of the herein described NHC ligands, preferably include one to four and in particular two ligands selected from hydrogen and halogen anions. Preferred halogen anions in this context are F$^-$ and Cl$^-$ and specifically Cl$^-$.

If in the process of the invention one of the aforementioned catalytic systems is used that comprises one of the phosphine ligands IV, V or VI and/or one of the NHC ligands VII or VIII, the dehydrogenation is preferably effected via the transfer-dehydrogenation in the presence of a reoxidant pursuant to step i). In this context the reoxidant is preferably selected from $C_3$-$C_6$-alkanones, $C_5$-$C_7$-cycoalkanones and benzaldehyde, and in particular from acetone, 3-pentanone, cyclohexanone and benzaldehyde.

According to a further embodiment of the present invention the dehydrogenation is carried out using a catalytic system comprising one ligand selected from the tridentate ligands of formulae IX and X, and in particular from those mentioned herein as preferred.

According to a further preferred embodiment of the invention the metal compound of the catalytic system according to the inventive process is a ruthenium compound, and in particular a ruthenium(II) compound.

Catalytic systems of the present invention that comprise a tridentate ligand of formulae IX or X are preferably selected from the ruthenium catalysts of the formulae XIa, XIb and XIc,

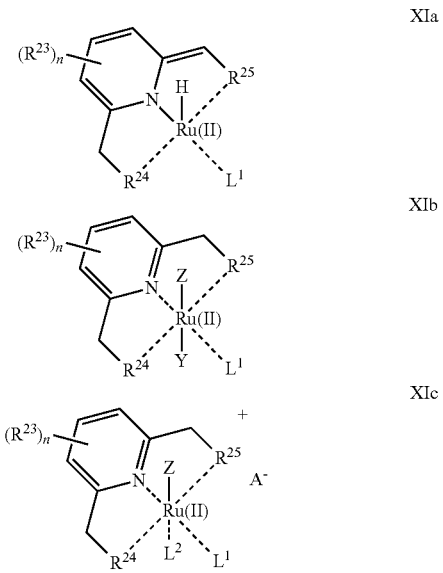

wherein
the variables $R^{23}$, n, $R^{24}$ and $R^{25}$ have the herein defined meanings and in particular those meanings mentioned as preferred, $L^1$ and $L^2$ are each independently selected from the group consisting of CO, $PR_3$, $P(OR)_3$, $NO^+$, $AsR_3$, $SbR_3$, $SR_2$, RCN, and RNC, where R has one of the meanings given herein, in particular one of the meanings mentioned as preferred, Y and Z are each independently selected from the group consisting of hydrogen and the anionic ligands $RC(O)O^-$, $CF_3C(O)O^-$, $RS(O)_2O^-$, $CF_3S(O)_2O^-$, $CN^-$, $HO^-$, $RO^-$, $R_2N^-$, $RS^-$, and $HS^-$, where R has one of the meanings given herein, in particular one of the meanings mentioned as preferred, and $A^-$ represents an anion with a single negative charge, such as e.g. fluoride, bromide, chloride, iodide, bicarbonate, $CN^-$, nitrate and $RC(O)O^-$, where R is as defined above.

Preferably, the ligand $L^1$ in the catalytic systems of the formulae XIa and XIb is selected from CO, $PR_3$ and $P(OR)_3$, where R is as defined herein and is in particular selected from $C_1$-$C_6$-alkyl, $C_3$-$C_7$-cycloalkyl, phenyl and benzyl.

Preferably, the ligands $L^1$ and $L^2$ in the catalytic systems of the formula XIc are each independently selected from the group consisting of CO, $PR_3$ and $P(OR)_3$, where R is as defined herein and is in particular selected from $C_1$-$C_6$-alkyl, $C_3$-$C_7$-cycloalkyl, phenyl and benzyl.

Preferably, the variables Y and Z in the catalytic systems of the formula XIb are each independently selected from the group consisting of hydrogen and the anionic ligands $RC(O)O^-$, $CF_3C(O)O^-$, $CN^-$, $HO^-$, $RO^-$ and $R_2N^-$, where R is as defined herein and is in particular selected from $C_1$-$C_8$-alkyl, $C_3$-$C_7$-cycloalkyl, phenyl and benzyl. More preferably Y and Z are both hydrogen.

Preferably, the variable Z in the catalytic systems of the formula XIc is selected from the group consisting of hydrogen and the anionic ligands $RC(O)O^-$, $CF_3C(O)O^-$, $CN^-$, $HO^-$, $RO^-$ and $R_2N^-$, where R is as defined herein and is in particular selected from $C_1$-$C_6$-alkyl, $C_3$-$C_7$-cycloalkyl, phenyl and benzyl. More preferably Z is hydrogen.

Among the ruthenium catalysts of the formulae XIa, XIb and XIc, including the ones mentioned herein as preferred, particular preference is given to those wherein the variables $R^{24}$ and $R^{25}$ are each independently selected from the group consisting of —$PR_2$, —$P(OR)_2$, —$NR_2$, —NHR, —$NH_2$, =NR, —SR, —SH, —S(=O)R and hetaryl, and specifically from —$PR_2$, —$NR_2$, —NHR and —$NH_2$, where the variable R in each case has one of the aforementioned meanings and in particular one of the meanings indicated as preferred. Even more preference is given those ruthenium catalysts XIa, XIb and XIc wherein $R^{24}$ and $R^2$ are each independently selected from the group consisting of —$P(C_1$-$C_8$-alkyl$)_2$, and specifically are both —P(tert-butyl)$_2$ Among the ruthenium catalysts of the formulae XIa, XIb and XIc, including the ones mentioned herein as preferred, particular preference is also given to those wherein the variables Y and Z are both hydrogen.

Among the ruthenium catalysts of the formulae XIa, XIb and XIc, including the ones mentioned herein as preferred, particular preference is also given to those wherein the variable n is 0.

Among the ruthenium catalysts of the formulae XIa, XIb and XIc, including the ones mentioned herein as preferred, particular preference is also given to those wherein the variable $L^1$ is CO.

Among the catalytic systems of the present invention that include a tridentate ligand of formulae IX or X preference is specifically given to the ruthenium catalysts of the formula XIb, wherein the variables $R^{23}$, n, $R^{24}$, $R^{25}$, $L^1$, Y and Z have the above defined meanings, in particular those mentioned as preferred.

If in the process of the invention one of the aforementioned ruthenium catalysts of formulae XIa, XIb and XIc is used as catalytic system, the dehydrogenation is preferably carried out reoxidant-free pursuant to step ii), i.e. by purely physical means. In this context the purely physical means are preferably selected from expelling the hydrogen by boiling the reaction mixture, by reducing the atmospheric pressure and/or by passing an auxiliary gas through the reaction mixture, and in particular consist of boiling the reaction mixture.

According to a preferred embodiment of the invention the catalytic system is a homogeneous catalytic system, i.e. the catalytic system is present in the reaction mixture of the dehydrogenation in dissolved or in suspended form. It is consequently preferred herein to use in the dehydrogenation a catalytic system that does not include a carrier or support material which is insoluble in the reaction mixture.

If the catalytic system comprises an iridium compound, then one or more ligands of the catalytic system for the dehydrogenation of the inventive process are preferably selected from cyclopentadienyls, the monodentate phosphines of formula IV, in particular those mentioned herein as preferred, the bidentate phosphines of formula V, in particular those mentioned herein as preferred, the NHC ligands of formulae VII or VIII, in particular those mentioned herein as preferred, and more preferably from cyclopentadienyls and NHC ligands of formulae VII or VIII. In this context even more preferred ligands are cyclolpentadienyl and pentamethylcyclopentadienyl.

According to another preferred embodiment of the invention one or more ligands of the intended catalytic system and the metal compound, in particular a ruthenium compound, as pre-catalyst are charged separately to the reaction vessel and the catalytic system used in the process of the invention is formed thereafter. Preferably, each ligand is added in an amount that at least approximately corresponds to the number of equivalents which are required, in relation to the molar amount of metal compound used, to form the intended metal catalyst. Each ligand is added in an amount of typically 80 to 120 wt-%, preferably 90 to 110 wt-% and specifically 95 to 105 wt-% of the amount that corresponds to the required equivalents.

According to yet another preferred embodiment of the invention the preformed metal complex that is employed as the catalytic system is charged to the reaction vessel.

The metal complex, in case it is preformed, or the metal compound of the catalytic system, in case of an in situ formation, is used in the process according to the invention preferably in an amount of 0.05 to 3.0 mol-%, more preferably in an amount of 0.1 to 2.0 mol-%, and especially in an amount of 0.15 to 1.5 mol-%, based on the amount of alkenol II and/or alkenol III used.

The reaction temperature of the dehydrogenation of the inventive process is determined by several factors, for example the reactivity of the reactants used and the type of the catalytic system selected, and can be determined by the person skilled in the art in the individual case, for example by simple preliminary tests. In general, the dehydrogenation of the process according to the invention is performed at a temperature in the range from 15 to 250° C., preferably in the range from 50 to 200° C., more preferably in the range from 70 to 170° C. and specifically in the range from 90 to 150° C.

According to an embodiment of the invention the dehydrogenation of the inventive process is carried out under reflux at the temperature of the boiling point of the reaction mixture. This embodiment is preferred in case the dehydrogenation is effected reoxidant-free in accordance to step ii), i.e. the formed hydrogen is removed by purely physical means.

The reaction pressure of the dehydrogenation of the inventive process depends on the solvent used, the reaction temperature, on whether the reaction vessel possesses a vent and also on which procedure for removing the hydrogen is chosen. In case the hydrogen formed during the dehydrogenation is removed via step i), i.e. by reaction with a reoxidant, a pressure of generally 1 to 15 bar and preferably of 1 to 10 bar is established during the reaction. However, in case the hydrogen is removed via step ii), i.e. by solely physical means, a pressure of generally 0.1 to 1.5 bar and preferably 0.3 to 1.1 bar is established during the reaction.

In case the process of the invention includes a transfer-dehydrogenation pursuant to step i), i.e. a reoxidant is employed for removing the hydrogen, the reoxidant is preferably used in an amount of 1 to 50 mol, more preferably of 2 to 45 mol, even more preferably of 2.5 to 40 mol and specifically of 3 to 35 mol, based in each case on 1 mol of the alkenol of formula II and/or the alkenol of formula III.

The starting compounds that include the catalytic system and an alkenol II and/or an alkenol III, need not be present in dissolved form for carrying out the novel process. The reaction usually gives optimum results even in suspension.

The intended product of the inventive process, the 2-alkenal of the formula I, is either removed from the reaction mixture during the dehydrogenation reaction, e.g. by distillation, preferably in a continuous manner, over the course of the reaction, or only after the reaction has been completed or terminated. In the latter case, after the end of the dehydration, the work-up of the obtained reaction mixture and the isolation of the 2-alkenal I are effected in a customary fashion, for example by centrifugation or filtration, e.g. filtration through a celite pad, by an aqueous extractive work-up, by removing the solvent and/or the 2-alkenal I via distillation, for instance under reduced pressure, or by a combination of these measures. Further purification can be effected, for example, by crystallization, distillation or chromatography.

Starting from alkanols of the formulae II and/or III the processes of the invention allow for the efficient preparation of 2-alkenals I in good yields and selectivities, while requiring only small amounts of ruthenium(II)- or iridium(I)-based catalysts. The inventive processes also include two alternative procedures for the effective removal of the potentially by-product forming hydrogen immediately after its generation.

The examples which follow illustrate the invention without restricting it. The GC analyses (GC: gas chromatography) were measured on a HP6890 machine, equipped with a FID detector and an Optima-FFAP column (50 m×0.32 mm, FD=0.5) using helium as carrier gas.

The invention is further illustrated by the following non-limiting examples.

EXAMPLES

I. Preparation of the Prenal Using the Transfer-Dehydrogenation Approach of the Invention I.a. Dehydrogenation of Prenol I.a.1 A solution of prenol (1.4 g, 16 mmol) and [Ru(Pn-Bu$_3$)$_4$(H)$_2$](144 mg, 0.16 mmol) in 40 mL 3-pentanone was stirred under reflux for 6 hours under inert conditions (argon atmosphere) in a Schlenk-flask (100 mL) equipped with a reflux condenser. After cooling to room temperature, the reaction mixture was analyzed by GC revealing the following percentage composition (based on the area percents of the respective peaks): prenol 2.7%, prenal 59.8%, 3-methyl-butan-1-ol 22.3%, isoprenol 8.5%, isovaleraldehyde 6.7%.

I.a.2 A solution of prenol (1.4 g, 16 mmol) and [Ru(PEt$_3$)$_4$(H)$_2$](115 mg, 0.16 mmol) in 40 mL 3-pentanone was stirred under reflux for 6 hours under inert conditions (argon atmosphere) in a Schlenk-flask (100 mL) equipped with a reflux condenser. After cooling to room temperature, the reaction mixture was analyzed by GC revealing the following percentage composition (based on the area percents of the respective peaks): prenol 8.1%, prenal 82.9%, 3-methyl-butan-1-ol 9.0%, isoprenol 0%, isovaleraldehyde 0%.

I.a.3 A solution of prenol (1.4 g, 16 mmol) and [Ru(Pn-Oct$_3$)$_4$(H)$_2$](120 mg, 0.08 mmol) in 40 mL 3-pentanone was stirred under reflux for 20 hours under inert conditions (argon atmosphere) in a Schlenk-flask (100 mL) equipped with a reflux condenser. After cooling to room temperature, the reaction mixture was analyzed by GC revealing the following percentage composition (based on the area percents of the respective peaks): prenol 12.6%, prenal 80.0%, 3-methyl-butan-1-ol 7.5%, isoprenol 0%, iso-valeraldehyde 0%.

I.a.4 A solution of prenol (1.0 g, 11.6 mmol) and [Ru(Pn-Oct$_3$)$_4$(H)$_2$](150 mg, 0.1 mmol) in 15 g cylohexanone was stirred at 120° C. for 20 hours under inert conditions (argon atmosphere) in a Schlenk-flask (50 mL) equipped with a reflux. After cooling to room temperature, the reaction mixture was analyzed by GC revealing the following percentage composition (based on the area percents of the respective peaks): prenal 3.0%, 3-methyl-butan-1-ol 0.2%, isoprenol 0%, iso-valeraldehyde 0.1%, cyclohexanone and prenol 88.3%, cyclohexanol 6.6%.

I.a.5 A solution of prenol (1.0 g, 11.6 mmol) and [Ru(Pn-Oct$_3$)$_4$(H)$_2$](200 mg, 0.13 mmol) in 15 g cylohexanone was stirred at 130° C. for 20 hours under inert conditions (argon atmosphere) in a Schlenk-flask (50 mL) equipped with a reflux condenser. After cooling to room temperature, the reaction mixture was analyzed by GC revealing the following percentage composition (based on the area percents of the respective peaks): prenal 2.3%, 3-methyl-butan-1-ol 0.3%, isoprenol 0%, iso-valeraldehyde 0.2%, cyclohexanone and prenol 86.8%, cyclohexanol 6.7%.

I.a.6 A solution of prenol (1.4 g, 16.0 mmol) and [Ru(Pn-Oct$_3$)$_4$(H)$_2$](120 mg, 0.08 mmol) in 40 mL acetone was stirred at 120° C. for 20 hours under inert conditions (argon atmosphere) in a pressure glass vessel (100 mL). After cooling to room temperature, the reaction mixture was analyzed by GC revealing the following percentage composition (based on the area percents of the respective peaks): prenol 17.7%, prenal 76.7%, 3-methyl-butan-1-ol 5.6%, isoprenol 0%, iso-valeraldehyde 0%.

I.a.7 A solution of prenol (4.0 g, 46.4 mmol) and [Ru(Pn-Octa)$_4$(H)$_2$](150 mg, 0.1 mmol) in 15 mL benzaldehyde was stirred at 120° C. for 20 hours under inert conditions (argon atmosphere) in a 100 ml Schlenk flask equipped with a reflux condenser. After cooling to room temperature, the reaction mixture was analyzed by GC revealing the following percentage composition (based on the area percents of the respective peaks): prenol 13.2%, prenal 86.8%, 3-methyl-butan-1-ol 0%, isoprenol 0%, isovaleraldehyde 0%.

I.b. Dehydrogenation of Isoprenol

I.b.1 A solution of isoprenol (1.0 g, 11.6 mmol) and [Ru(Pn-Oct$_3$)$_4$(H)$_2$](200 mg, 0.13 mmol) in 15 g cylohexanone was stirred at 120° C. for 20 hours under inert conditions (argon atmosphere) in a Schlenk-flask (50 mL) equipped with a reflux condenser. After cooling to room temperature, the reaction mixture was analyzed by GC revealing the following percentage composition (based on the area percents of the respective peaks): prenol 0%, prenal 62.2%, 3-methyl-butan-1-ol 0%, isoprenol 37.1%, isovaleraldehyde 0%.

I.b.2 A solution of isoprenol (4.0 g, 46.4 mmol) and [Ru(PnOct$_3$)$_4$(H)$_2$](150 mg, 0.1 mmol) in 15 g cylohexanone was stirred at 120° C. for 20 hours under inert conditions (argon atmosphere) In a Schlenk-flask (50 mL) equipped with a reflux condenser. After cooling to room temperature, the reaction mixture was analyzed by GC revealing the following percentage composition (based on the area percents of the respective peaks): prenal 11.6%, 3-methyl-butan-1-ol 1.3%, isoprenol 0.4%, iso-valeraldehyde 0.5%, cyclohexanone and prenol 63.8%, cyclohexanol 19.3%.

II. Preparation of the Prenal Using the Reoxidant-Free Dehydrogenation of the Invention II.a. Dehydrogenation of Prenol II.a.1 A solution of prenol (1.0 g, 11.6 mmol), [Ru(PPh$_3$)$_3$(H)$_2$(CO)](150 mg, 0.16 mmol) and 2,6-bis(di-tert-butylphosphinomethyl)pyridine (64 mg, 0.16 mmol) in 20 mL xylene was refluxed with stirring for 16 hours under inert conditions (argon atmosphere) in a Schlenk-flask (50 mL) equipped with a reflux condenser. After cooling to room temperature, the reaction mixture was analyzed by GC revealing the following percentage composition (based on the area percents of the respective peaks): prenol 7.5%, prenal 64.6%, 3-methyl-butan-1-ol 12.4%, isoprenol 6.8%, iso-valeraldehyde 8.7%.

II.a.2 A solution of prenol (172 mg, 2 mmol), [Ru(PPh$_3$)$_3$(H)$_2$(CO)](36 mg, 0.04 mmol) and 2,6-bis(di-tert-butylphosphinomethyl)pyridine (16 mg, 0.04 mmol) in 10 mL toluene was refluxed with stirring for 16 hours under inert conditions (argon atmosphere) in a Schlenk-flask (50 mL) equipped with a reflux condenser. After cooling to room temperature, the reaction mixture was analyzed by GC revealing the following percentage composition (based on the area percents of the respective peaks): prenol 45.1%, prenal 54.9%, 3-methyl-butan-1-ol 0%, isoprenol 0%, iso-valeraldehyde 0%.

II.a.3 A solution of prenol (172 mg, 2 mmol), [Ru(COD)Cl₂]₂ (14 mg, 0.025 mmol), 1-methyl-3-butylimidazolium-chloride (8.7 mg, 0.05 mmol), potassium tert-butylate (16.8 mg, 0.15 mmol) and tricyclohexylphosphine (14 mg, 0.05 mmol) in 10 mL toluene was refluxed with stirring for 12 hours under inert conditions applying a slow flow of argon. After cooling to room temperature, the reaction mixture was analyzed by GC revealing the following percentage composition (based on the area percents of the respective peaks): isoprenol 8.6%, prenal 31.4%, 3-methyl-butan-1-ol 60.0%.

II.a.4 A solution of prenol (688 mg, 8 mmol), [Ru(Pn-Bu₃)₄(H)₂](144 mg, 0.16 mmol) and 1,2-bis-(dicyclohexylphosphino)-ethane (72 mg, 0.16 mmol) in 20 mL toluene was refluxed with stirring for 12 hours under inert conditions applying a slow flow of argon. After cooling to room temperature, the reaction mixture was analyzed by GC revealing the following percentage composition (based on the area percents of the respective peaks): prenol 3.3%, isoprenol 2.2%, prenal 46.1%, isovaleraldehyde 9.4%, 3-methyl-butan-1-ol 38.9%.

II.a.5 A solution of prenol (172 mg, 2 mmol) and [Ru(Pn-Bu₃)₄(H)₂](36 mg, 0.04) in 20 mL toluene was refluxed with stirring for 12 hours under inert conditions applying a slow flow of argon. After cooling to room temperature, the reaction mixture was analyzed by GC revealing the following percentage composition (based on the area percents of the respective peaks): prenal 44.6%, isovaleraldehyde 21.4%, 3-methyl-butan-1-ol 33.9%.

II.b. Dehydrogenation of Isoprenol

II.b.1 A solution of isoprenol (1.0 g, 11.6 mmol), [Ru(PPh₃)₃(H)₂(CO)](150 mg, 0.16 mmol) and 2,6-bis(di-ter-butylphosphinomethyl)pyridine (64 mg, 0.16 mmol) in 20 mL xylene was refluxed with stirring for 16 hours under inert conditions (argon atmosphere) in a Schlenk-flask (50 mL) equipped with a reflux condenser. After cooling to room temperature, the reaction mixture was analyzed by GC revealing the following percentage composition (based on the area percents of the respective peaks): prenol 11.4%, Prenal 31.9%, 3-Methyl-Butan-1-ol 7.0%, Isoprenol 49.8%, iso-Valeraldehyd 0%.

II.b.2 A solution of isoprenol (344 mg, 4 mmol), [Ru(COD)Cl₂]₂ (14 mg, 0.025 mmol), 1-methyl-3-butylimidazolium-chloride (9 mg, 0.05 mmol), potassium tert-butylate (17 mg, 0.15 mmol) and tricyclohexylphosphine (14 mg, 0.05 mmol) in 10 mL toluene was refluxed with stirring for 12 hours under inert conditions applying a slow flow of argon. After cooling to room temperature, the reaction mixture was analyzed by GC revealing the following percentage composition (based on the area percents of the respective peaks): prenol 8.8%, isoprenol 52.2%, prenal 9.6%, 3-methyl-butan-1-ol 29.4%.

The invention claimed is:

1. A process for preparing 2-alkenals of the formula I

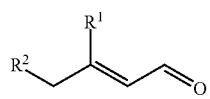

in which
R¹ is hydrogen or $C_1$-$C_4$-alkyl; and
R² is hydrogen, $C_1$-$C_{12}$-alkyl, $C_2$-$C_{12}$-alkenyl, $C_4$-$C_8$-cycloalkyl or $C_6$-$C_{10}$-aryl, wherein $C_1$-$C_{12}$-alkyl and $C_1$-$C_{12}$-alkenyl are optionally substituted with $C_5$-$C_7$-cycloalkyl or $C_5$-$C_7$-cycloalkenyl;

comprising dehydrogenating an alkenol of the formula II, an alkenol of the formula III or a mixture thereof,

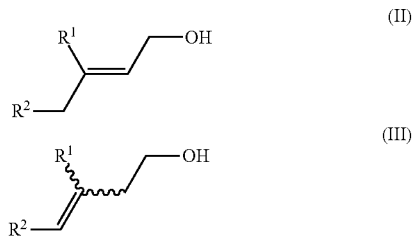

wherein
R¹ and R² are each as defined above,
wherein the alkenol II, the alkenol III or a mixture thereof is brought into contact with a catalytic system comprising at least one ligand and a metal compound selected from the group consisting of ruthenium(II) compounds, iridium(I) compounds, and combinations thereof, and
wherein hydrogen formed during the dehydrogenation is removed from the reaction mixture by:
i) reaction with a reoxidant selected from the group consisting of $C_3$-$C_{12}$-alkanones, $C_4$-$C_9$-cycloalkanones, benzaldehyde and mixtures thereof; and/or
ii) purely physical means.

2. The process according to claim 1, wherein R¹ is methyl and R² is hydrogen.

3. The process according to claim 1, wherein the substituent R¹ of the alkenol of formula III is in the cis-position related to the substituent R².

4. The process according to claim 1, wherein the alkenol subjected to the dehydrogenation is selected from compounds of the formula II.

5. The process according to claim 1, wherein the alkenol subjected to the dehydrogenation is selected from compounds of the formula III.

6. The process according to claim 1, wherein the at least one ligand of the catalytic system is selected from the group consisting of monodentate, bidentate and tridentate phosphine ligands.

7. The process according to claim 6, wherein the catalytic system comprises one to six ligands selected from the group consisting of monodentate phosphines of the formula IV and bidentate phosphines of the formula V,

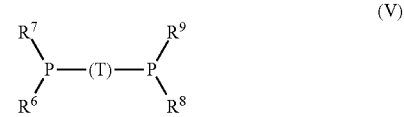

wherein
R³ to R⁹ are each independently $C_1$-$C_{12}$-alkyl, $C_3$-$C_{12}$-cycloalkyl, adamantyl, aryl-$C_1$-$C_2$-alkyl, ferrocenyl or aryl, where aryl is optionally substituted by $C_1$-$C_4$-alkyl, $C_1$-$C_4$-alkoxy, fluorine or chlorine, and
T is linear $C_2$-$C_5$-alkanediyl, which optionally is substituted by $C_1$-$C_8$-alkyl or $C_3$-$C_6$-cycloalkyl and optionally is part of one or two mono- or bicyclic rings which are unsubstituted or substituted.

8. The process according to claim 7, wherein
R$^3$ to R$^9$ are each independently C$_1$-C$_{10}$-alkyl or C$_4$-C$_8$-cycloalkyl, and
T is linear C$_2$-C$_5$-alkanediyl which may optionally be substituted by C$_1$-C$_4$-alkyl.

9. The process according to claim 1, wherein the at least one ligand of the catalytic system is selected from N-heterocyclic carbenes of the formulae VII and VIII,

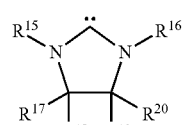
(VII)

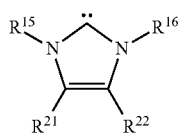
(VIII)

wherein
R$^{15}$ and R$^{16}$ are each independently C$_1$-C$_{10}$-alkyl, aryl or hetaryl, where aryl and hetaryl may optionally carry 1, 2, 3 or 4 substituents selected from C$_1$-C$_8$-alkyl and C$_3$-C$_7$-cycloalkyl,
R$^{17}$, R$^{18}$, R$^{19}$ and R$^{20}$ are each independently hydrogen, C$_1$-C$_8$-alkyl or aryl, or two of the radicals R$^{17}$, R$^{18}$, R$^{19}$ and R$^{20}$ form a saturated five- to seven-membered ring, where the two other radicals are each independently hydrogen or methyl, and
R$^{21}$ and R$^{22}$ are each independently hydrogen, C$_1$-C$_8$-alkyl or aryl, or R$^{21}$ and R$^{22}$, together with the heterocyclic moiety to which they are bonded, are a fused ring system with 1 or 2 aromatic rings.

10. The process according to claim 9, wherein the catalytic system comprises one or two ligands selected from N-heterocyclic carbenes of the formula VIII, where
R$^{15}$ and R$^{16}$ are each independently C$_1$-C$_{10}$-alkyl or phenyl optionally carrying 1 or 2 substituents selected from C$_1$-C$_8$-alkyl, and
R$^{21}$ and R$^{22}$ are both hydrogen.

11. The process according to claim 6, wherein the catalytic system comprises two ligands selected from hydrogen and halogen anions.

12. The process according to claim 1, wherein the metal compound of the catalytic system is selected from ruthenium (II) compounds.

13. The process according to claim 5, wherein the hydrogen is removed from the reaction mixture according to step i).

14. The process according to claim 1, wherein catalytic system is selected from the ruthenium catalysts of formulae XIa, XIb and XIc,

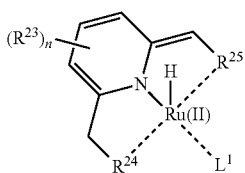
XIa

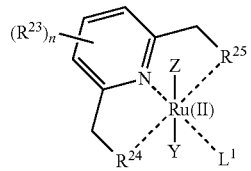
XIb

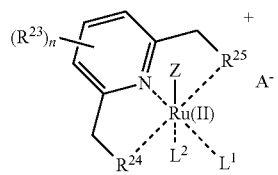
XIc wherein
R$^{23}$ is selected from the group consisting halogen, NO$_2$, CN, C$_1$-C$_{10}$-alkyl, C$_3$-C$_9$-cycloalkyl, aryl, hetaryl, C$_3$-C$_8$-heterocyclyl, C$_1$-C$_{10}$-alkoxy, (C$_1$-C$_6$-alkoxy)carbonyl, (C$_1$-C$_6$-alkylamino)carbonyl, aryl-(C$_1$-C$_6$)-alkyl, and optionally spacer-modified inorganic or organic support;
n is 0, 1, 2 or 3;
R$^{24}$ and R$^{25}$ are each independently selected from the group consisting of
—PR$_2$, —P(OR)$_2$, —NR$_2$, —NHR, —NH$_2$, =NR, —SR, —SH, —S(=O)R, hetaryl, —AsR$_2$, —SbR$_2$, a carbene of the formula: CRR', and a carbene of the formula

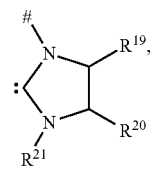

wherein
R, R$^{19}$, R$^{20}$ and R$^{21}$ are independently of each other selected from the group consisting of C$_1$-C$_{10}$-alkyl, C$_3$-C$_9$-cycloalkyl, aryl, aryl-(C$_1$-C$_6$)-alkyl, C$_3$-C$_8$-heterocyclyl and hetaryl,
R' is selected from the group consisting of C$_1$-C$_{10}$-alkanediyl, C$_3$-C$_9$-cycloalkanediyl, arenediyl, aryl-(C$_1$-C$_6$)-alkanediyl, C$_3$-C$_8$-heterocyclene and hetarenediyl, and
# is the attachment point to the remainder of the molecule;
L$^1$ is selected from the group consisting of CO, PR$_3$, P(OR)$_3$, NO$^+$, AsR$_3$, SbR$_3$, SR$_2$, RCN, and RNC, where R is as defined herein above;
L$^2$ is defined as ligand L$^1$ above or is absent;
Y and Z are each independently selected from the group consisting of hydrogen and the anionic ligands RC(O)O$^-$, CF$_3$C(O)O$^-$, RS(O)$_2$O$^-$, CF$_3$S(O)$_2$O$^-$, CN$^-$, HO$^-$, RO$^-$, R$_2$N$^-$, RS$^-$, and HS$^-$, where R is as defined herein above; and
A$^-$ represents an anion with a single negative charge.

15. The process according to claim 14, wherein R$^{24}$ and R$^{25}$ are each independently selected from the group consisting of —P(C$_1$-C$_6$-alkyl)$_2$.

16. The process according to claim 14, wherein Y and Z are both hydrogen, n is 0 and L$^1$ is CO.

17. The process according to claim 4, wherein the hydrogen is removed from the reaction mixture according to step ii).

18. The process according to claim 7, wherein
    $R^3$ to $R^9$ are each independently ethyl, 1-butyl, sec-butyl, 1-octyl or cyclohexyl, and
    T is ethan-1,2-diyl, propan-1,3-diyl, propan-1,2-diyl, butan-1,4-diyl or butan-1,3-diyl.

19. The process according to claim 14, wherein $R^{24}$ and $R^{25}$ are both —P(tert-butyl)$_2$.

* * * * *